US006967234B2

(12) United States Patent
Nathan

(10) Patent No.: US 6,967,234 B2
(45) Date of Patent: *Nov. 22, 2005

(54) ALKYD-LACTONE COPOLYMERS FOR MEDICAL APPLICATIONS

(75) Inventor: Aruna Nathan, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 89 days.

This patent is subject to a terminal disclaimer.

(21) Appl. No.: 10/322,132

(22) Filed: Dec. 18, 2002

(65) Prior Publication Data

US 2004/0122205 A1 Jun. 24, 2004

(51) Int. Cl.$^7$ .................. C08G 63/02; C08G 63/00; A61F 2/00; A61K 9/14
(52) U.S. Cl. .................. 528/272; 528/288; 528/289; 528/290; 528/296; 528/299; 528/306; 424/426; 424/486
(58) Field of Search ................ 528/272, 288, 528/289, 290, 296, 299, 306, 354, 355, 359; 424/426, 486, 430, 408; 525/411, 437, 509, 511, 413, 444; 428/357, 359, 364, 383, 36.1

(56) References Cited

U.S. PATENT DOCUMENTS

| 2,895,930 A | 7/1959 | Milton |
| 3,278,464 A | 10/1966 | Boyer et al. |
| 3,806,479 A | 4/1974 | Cunningham et al. |
| 3,978,203 A | 8/1976 | Wise |
| 3,997,512 A | 12/1976 | Casey et al. |
| 4,048,256 A | 9/1977 | Casey et al. |
| 4,076,798 A | 2/1978 | Casey et al. |

(Continued)

FOREIGN PATENT DOCUMENTS

| DE | 1694845 A | 8/1971 |
| EP | 0422209 B1 | 3/1995 |
| EP | 841361 A1 | 5/1995 |
| EP | 747072 A | 12/1996 |
| EP | 1270024 A | 1/2003 |
| EP | 1348451 A | 10/2003 |
| EP | 1369136 A | 12/2003 |
| EP | 1374860 A | 1/2004 |
| GB | 630924 A | 10/1949 |
| WO | WO 88/03785 A1 | 6/1988 |
| WO | WO 89/08694 A1 | 9/1989 |
| WO | WO 90/12604 A1 | 11/1990 |
| WO | WO 92/12645 A1 | 8/1992 |
| WO | WO 93/08850 A1 | 5/1993 |
| WO | WO 94/25079 A1 | 11/1994 |
| WO | WO 94/15079 A1 | 11/1995 |
| WO | WO 95/33821 A1 | 12/1995 |
| WO | WO 97/09367 | 3/1997 |
| WO | WO 97/23606 A1 | 7/1997 |
| WO | WO 95/22318 A1 | 8/1997 |
| WO | WO 99/29303 A1 | 8/1999 |
| WO | WO 00/02950 A1 | 1/2000 |
| WO | WO 00/35511 A | 8/2000 |
| WO | WO 00/44808 A1 | 8/2000 |
| WO | WO 01/07486 A1 | 2/2001 |
| WO | WO 01/76649 A | 10/2001 |

OTHER PUBLICATIONS

U.S. Appl. No. 10/112,554, A. Nathan, et al.
U.S. Appl. No. 10/162,933, A. Nathan.
U.S. Appl. No. 10/178,970, A. Nathan.
U.S. Appl. No. 10/183,260, J. Rosenbatt, et al.
U.S. Appl. No. 10/322,177, S.C. Arnold.
U.S. Appl. No. 10/325,768, A. Nathan
U.S. Appl. No. 10/323,367, A. Nathan.
U.S. Appl. No. 10/322,154, A. Nathan.
U.S. Appl. No. 10/322,117, A. Nathan.
U.S. Appl. No. 10/112,201, A. Nathan, et al.
EPO Search Report dated Dec. 15, 2003 for EPO Appl. No. EP 03 25 1999.
Database WPI Week 199430 Derwent Publications Ltd., London, GB; and 1994–248859 XP002256761 & WO 94 15591 A. (Hisamitsu), Jul. 12, 1994, abstract.
Mark H.F.: "Alkyd Resins", Encyclopedia of Polmer Sience and Engineering. A to Amorphous Polymers, New York, J. Wiley & Sons, US. vol. 1, pp. 644–648 xP002035651 the whole document*.
Emino Koyama, Fumio Sanda, and Takeshi Endo, "Synthesis of Poly(ester–amide)s Derived from Optically Active Amino Alcohols," Macromol. Symp., 122, 275–280 (1997).
Emiko Koyama, Fumio Sanda, and Takeshi Endo, "Polycondensations of Hydroxycarboxylic Acids Derived from Optically Active Aminoalcohols and Acid Anhydrides—Syntheses of Functional Poly(ester–amide)s," Journal of Polymer Science: Part A: Polymer Chemistry 35, 345–352 (1997).
Donald L. Elbert, Alison B. Pratt, Matthias P. Lutolf, Sven Halstenberg, Jeffrey A. Hubbell, "Protein Delivery from Materials Formed by Self–selective Conjugate Addition Reactions," Journal of Controlled Release, 76, 11–25 (2001).
EPO Search Reports dated Apr. 22, Apr. 23, another Apr. 23, & Apr. 28, 2004.
Brian Parkyn F. Lamb and B. V. Clifton, "Polyesters vol. 2 Unsaturated Polyesters and Polyester Plasticisers," London Iliffie Books Ltd., New York American Elsevier ublishing Company, Inc., 1967 pp. 107–122.
Temple C. Patton, "Alkyd Resin Technology–Formulating Techniques and Allied Calculations," Interscience Publishers, a of John Wiley and Sons, New York–London 1962, pp. 13–31.

*Primary Examiner*—P. Hampton Hightower

(57) ABSTRACT

The present invention is directed to biodegradable, biocompatible polymers that are the reaction product of a polybasic acid or derivative thereof, a monoglyceride and a lactone monomer, as well as medical devices and compositions containing such polymers.

44 Claims, No Drawings

U.S. PATENT DOCUMENTS

| | | | |
|---|---|---|---|
| 4,095,600 A | 6/1978 | Casey et al. | |
| 4,118,470 A | 10/1978 | Casey et al. | |
| 4,122,129 A | 10/1978 | Casey et al. | |
| 4,163,073 A | 7/1979 | Pepe et al. | |
| 4,384,975 A | 5/1983 | Fong | |
| 4,419,139 A | 12/1983 | Gooch et al. | |
| 4,568,559 A | 2/1986 | Nuwayser et al. | |
| 5,137,743 A | 8/1992 | Zaks et al. | |
| 5,155,246 A | 10/1992 | Naskar et al. | |
| 5,219,980 A | 6/1993 | Swidler | |
| 5,306,311 A | 4/1994 | Stone et al. | |
| 5,308,623 A | 5/1994 | Fues et al. | |
| 5,360,626 A | 11/1994 | Iyengar et al. | |
| 5,411,554 A | 5/1995 | Sopelianos et al. | |
| 5,442,033 A | 8/1995 | Bezwada | |
| 5,464,929 A | 11/1995 | Bezwada et al. | |
| 5,525,646 A | 6/1996 | Lundgren et al. | |
| 5,599,852 A | 2/1997 | Sopelianos et al. | |
| 5,607,687 A | 3/1997 | Bezwada et al. | |
| 5,618,552 A | 4/1997 | Bezwada et al. | |
| 5,628,993 A | 5/1997 | Yamagata et al. | |
| 5,631,015 A | 5/1997 | Bezwada et al. | |
| 5,653,992 A | 8/1997 | Bezwada et al. | |
| 5,670,478 A | 9/1997 | Stuchlik et al. | |
| 5,698,213 A | 12/1997 | Jamiolkowski et al. | |
| 5,700,583 A | 12/1997 | Jamiolkowski et al. | |
| 5,725,881 A | 3/1998 | Buchholz et al. | |
| 5,728,752 A | 3/1998 | Scopelianos et al. | |
| 5,750,100 A | 5/1998 | Yamagata et al. | |
| 5,753,234 A | 5/1998 | Lee et al. | |
| 5,824,333 A | 10/1998 | Scopelianos et al. | |
| 5,859,150 A | 1/1999 | Jamiolkowski et al. | |
| 5,998,552 A * | 12/1999 | Gruber et al. | 525/450 |
| 6,074,660 A | 6/2000 | Jamiolkowski et al. | |
| 6,100,346 A | 8/2000 | Jamiolkowski et al. | |
| 6,110,501 A | 8/2000 | Redding, Jr. et al. | |
| 6,114,458 A | 9/2000 | Hawker et al. | |
| 6,120,787 A | 9/2000 | Gustafsson et al. | |
| 6,121,398 A | 9/2000 | Wool et al. | |
| 6,147,168 A | 11/2000 | Jamiolkowski et al. | |
| 6,224,894 B1 | 5/2001 | Jamiolkowski et al. | |
| 6,251,435 B1 | 6/2001 | Jamiolkowski et al. | |
| 6,268,329 B1 | 7/2001 | Markussen | |
| 6,335,383 B1 | 1/2002 | Scopelianos et al. | |
| 2001/0007771 A1 | 7/2001 | Sullivan et al. | |
| 2001/0021377 A1 | 9/2001 | Jamiolkowski et al. | |
| 2002/0037301 A1 | 3/2002 | De La Poterie | |
| 2003/0185752 A1 * | 10/2003 | Nathan et al. | 424/1.11 |
| 2003/0236310 A1 * | 12/2003 | Nathan et al. | 514/772.4 |

* cited by examiner

ALKYD-LACTONE COPOLYMERS FOR MEDICAL APPLICATIONS

FIELD OF THE INVENTION

The present invention relates to biodegradable, biocompatible polymers for use in pharmaceutical and medical applications and to compositions and medical devices containing such polymers.

BACKGROUND OF THE INVENTION

Both natural and synthetic polymers, including homopolymers and copolymers, which are both biocompatible and biodegradable in vivo are known for use in the manufacture of medical devices that are implanted in body tissue and that are absorbed or passed by the body over time. Examples of such medical devices include suture anchor devices, sutures, staples, surgical tacks, clips, plates, screws, drug delivery devices, adhesion prevention films and foams, and tissue adhesives.

Natural polymers may include catgut, cellulose derivatives and collagen. Natural polymers typically are absorbed by the body after an enzymatic degradation process of the polymers in the body.

Synthetic polymers may include aliphatic polyesters, polyanhydrides and poly(orthoester)s. Such polymers typically degrade by a hydrolytic mechanism in the body and then are absorbed by the body. Such synthetic absorbable polymers include homopolymers, such as poly(glycolide), poly(lactide), poly(e-caprolactone), poly(trimethylene carbonate) and poly(p-dioxanone), and copolymers, such as poly(lactide-co-glycolide), poly(e-caprolactone-co-glycolide), poly(glycolide-co-trimethylene carbonate), poly(alkylene diglycolate), and polyoxaesters. The polymers may be statistically random copolymers, segmented copolymers, block copolymers or graft copolymers.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

There is a great need for polymers for use in drug delivery and medical devices, where the polymers have both low melting temperatures and low viscosities upon melting, thus permitting for solvent-free processing techniques in preparation of medical devices and compositions, can crystallize rapidly, and biodegrade within 6 months. There is also a need for polymers that can form injectable microdispersions for delivery of unstable drugs such as proteins.

SUMMARY OF THE INVENTION

The present invention is directed to synthetic, biodegradable, biocompatible polymers comprising the reaction product of a polybasic acid or derivative thereof, a monoglyceride and a lactone, and to compositions for use in medical applications and medical devices containing such polymers.

DETAILED DESCRIPTION OF THE INVENTION

Alkyd polymers have been prepared by several known methods. For example, alkyd-type polymers were prepared by Van Bemmelen (*J. Prakt. Chem.*, 69 (1856) 84) by condensing succinic anhydride with glycerol. In the "Fatty Acid" method (see Parkyn, et al. *Polyesters* (1967), Iliffe Books, London, Vol. 2 and Patton, In: *Alkyd Resins Technology*, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The synthetic, biodegradable, biocompatible polymers utilized in the present invention are the reaction product of a polybasic acid or derivative thereof, a monoglyceride, and a lactone, and may be classified as alkyd-lactone copolymers. Preferably, the polymers of the present invention are prepared by the polycondensation first of a polybasic acid, or derivative thereof, with a monoglyceride to form an alkyd polyester prepolymer. The monoglyceride comprises reactive hydroxy groups and fatty acid groups. The alkyd polyester prepolymer is reacted with one or more lactone monomers to form the alkyd-lactone copolymers of the present invention. The expected hydrolysis byproducts are glycerol, hydroxyacid(s), dicarboxylic acid(s), and fatty acid(s), all of which are biocompatible. The polymers comprise an aliphatic polyester backbone with pendant fatty acid ester groups on the alkyd polyester block. Long chain saturated fatty acids result in polymers that are solids and that exhibit relatively low melting points, e.g. between about 25° C. and 70° C. Alternatively, use of unsaturated fatty acids or short chain fatty acids results in liquid polymers. As used herein, a liquid polymer is a polymer with a melt temperature of less than about 25° C., preferably less than about 20° C.

The solid polymers and liquid polymers can be blended to form injectable microdispersions. The microdispersions can be formed by physically blending liquid polymers of the present invention with finely ground solid polymers of the present invention, or by grinding a suspension of large pieces of the solid polymers using the liquid polymer as a lubricant, until the desired particle size distribution is obtained.

Generally, the solid polymers will have an average particle diameter of less than about 500 microns and preferably less than 50 microns. It is currently preferred to mix the finely ground solid polymer and liquid polymer and raise the temperature of the mixture to a temperature sufficient to melt the solid polymer (melt blending). Melt blending is preferred because it simplifies the mixing operation involved in producing the microdispersion. It is desirable to avoid excessive heating during melt blending to avoid transesterification of the polymers.

Monoglycerides that may be used to prepare the polymers utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monostearoyl glycerol, monopalmitoyl glycerol and monomyrisitoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

Suitable lactone-derived repeating units may be generated from the following monomers, including but not limited to lactone monomers selected from the group consisting of glycolide, d-lactide, l-lactide, meso-lactide, epsilon-caprolactone, para-dioxanone, trimethylene carbonate, 1,4 dioxepan-2-one and 1,5 dioxepan-2-one.

In certain embodiments of the invention, the alkyd polyester prepolymer may be prepared from the polybasic acid or derivative thereof, the monoglyceride and, additionally, at least one additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

In preparing the polymers utilized in the present invention, the particular chemical and mechanical properties required of the polymer for a particular use must be considered. For example, changing the chemical composition can vary the physical and mechanical properties, including absorption times. Copolymers can be prepared by using mixtures of diacids, different monoalkanoyl glycerides and different lactones to provide a desired set of properties. Similarly, blends of two or more alkyd-lactone copolymers may be prepared to tailor properties for different applications.

Copolymers containing other linkages in addition to an ester linkage also may be synthesized. For example, ester-amides, ester-carbonates, ester-anhydrides and ester urethanes may be used, to name a few.

Multifunctional monomers may be used to produce crosslinked polymeric networks. Alternatively, double bonds may be introduced by using monoglycerides or diacids containing at least one double bond to allow photo-crosslinking. Hydrogels may be prepared using this approach provided the polymer is sufficiently water soluble or swellable.

Functionalized polymers can be prepared by appropriate choice of monomers. Polymers having pendant hydroxyls can be synthesized using a hydroxy acid such as malic or tartaric acid in the synthesis. Polymers with pendent amines, carboxyls or other functional groups also may be synthesized.

A variety of biologically active substances, hereinafter referred to as bioactive agents, can be covalently attached to these functional polymers by known coupling chemistry to provide sustained release of the bioactive agent. As used herein, bioactive agent is meant to include those substances or materials that have a therapeutic effect on mammals, e.g. pharmaceutical compounds. By effective amount of a bioactive agent, it is meant that the composition comprises the bioactive agent in minimum amounts that are effective in providing the therapeutic effect that the bioactive agent is intended to provide.

In another embodiment, the polymers of the present invention may be endcapped in a variety of ways to obtain the desired properties. Endcapping reactions convert the terminal and pendant hydroxyl groups and terminal carboxyl groups into other types of chemical moieties. Typical endcapping reactions include, but are not limited to, alkylation and acylation reactions using common reagents such as alkyl, alkenyl, or alkynyl halides and sulfonates, acid chlorides, anhydrides, mixed anhydrides, alkyl and aryl isocyanates, and alkyl and aryl isothiocyanates. Endcapping reactions can impart new functionality to the polymers of this invention. For instance, when acryloyl or methacryloyl, chloride is used to endcap these polymers, acrylate or methacrylate ester groups, respectively, are created that subsequently can be polymerized to form a crosslinked network. One skilled in the art, once having the benefit of the disclosure herein, will be able to ascertain particular properties of the liquid polymers required for particular purposes and readily prepare liquid polymers that provide such properties.

The polymerization of the polyether alkyds preferably is performed under melt polycondensation conditions in the presence of an organometallic catalyst at elevated temperatures. The organometallic catalyst preferably is a tin-based catalyst, e.g. stannous octoate. The catalyst preferably will be present in the mixture at a mole ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 180° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

The alkyd polyester prepolymer prepared using conditions described above may then be reacted with at least one lactone monomer or lactone prepolymer. The mixture then would be subjected to the desired conditions of temperature and time to copolymerize the alkyd polyester prepolymer with the lactone monomer. Generally, this reaction mixture will be maintained at about 190° C. The polymerization reaction can be allowed to proceed at this temperature until the desired molecular weight and percent conversion is achieved for the copolymer, which typically will take from about 15 minutes to 24 hours.

The molecular weight of the prepolymer, as well as its composition, can be varied depending on the desired characteristic that the prepolymer is to impart to the copolymer. Those skilled in the art will recognize that the alkyd-lactone copolymers described herein can also be made from mixtures of more than one monoglyceride, dicarboxylic acid, and lactone monomer.

The polymers, copolymers and blends of the present invention can be crosslinked to affect mechanical properties. Crosslinking can be accomplished by the addition of crosslinking enhancers, irradiation, e.g. gamma-irradiation, or a combination of both. In particular, crosslinking can be used to control the amount of swelling that the materials of this invention experience in water.

One of the beneficial properties of the alkyd-lactone copolymers of this invention is that the ester linkages are hydrolytically unstable and, therefore, the polymer is biodegradable because it readily breaks down into small segments when exposed to moist body tissue. In this regard, while it is envisioned that co-reactants could be incorporated into the reaction mixture of the polybasic acid and the diol and subsequent reaction with lactone monomer for the formation of the alkyd-lactone copolymers, it is preferable that the reaction mixture does not contain a concentration of any co-reactant that would render the subsequently prepared polymer nonbiodegradable. Preferably, the reaction mixture is substantially free of any such co-reactants if the resulting polymer is rendered nonbiodegradable.

In one embodiment of the invention, the alkyd-lactone copolymers of the present invention can be used as a pharmaceutical carrier in a drug delivery matrix. Solid alkyd-lactone copolymers could be used to coat or encapsulate a bioactive agent. Alternatively, an effective amount of a bioactive agent could be mixed with injectable microdispersions of solid polymer and liquid polymer. Such a microdispersion would be particularly suitable for unstable drugs such as proteins.

The variety of bioactive agents that can be used in conjunction with the polymers of the invention is vast. The bioactive agents are present in compositions and/or medical devices of the present invention in effective amounts. By effective amount, it is meant that the agents are present in amounts effective to provide the desired or necessary therapeutic effect of the agent, depending on the particular composition or device and the particular application of same. One skilled in the art, once having the benefit of this disclosure, will be able to ascertain the effective amount for the particular application.

In general, bioactive agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, growth factors, polysaccharides, glycoproteins or lipoproteins; oligonucleotides; antibodies; antigens; cholinergics; chemotherapeutics; hemostatics; clot dissolving agents; radioactive agents; and cystostatics.

Rapamycin, risperidone, and erythropoietin are preferred bioactive agents that may be used in drug delivery matrices of the present invention.

The drug delivery matrix may be administered in any suitable dosage form such as oral, parenteral, pulmonary, buccal, nasal, ocular, topical, vaginal routes, or as a suppository. Bioerodible particles, ointments, gels, creams, and similar soft dosage forms adapted for the administration via the above routes may also be formulated. Other modes of administration, e.g. transdermal, and compositional forms, e.g. more rigid transdermal forms, are within the scope of the invention as well.

Parenteral administration of a bioerodible composition of the invention can be effected by either subcutaneous or intramuscular injection. The bioactive agent could be encapsulated in particles made of the solid polymer. Alternatively, parenteral formulations of the copolymer may be formulated by mixing one or more pharmaceuticals with a liquid copolymer or microdispersion. Other suitable parenteral additives may be formulated with the copolymer and pharmaceutical active. However, if water is to be used it should be added immediately before administration. Bioerodible ointment, gel or cream may also be injected as is or in combination with one or more suitable auxiliary components as described below. Parenteral delivery is preferred for administration of proteinaceous drugs such as growth factors, growth hormone, or the like.

The bioerodible ointments, gels and creams of the invention will include an ointment, gel or cream base comprising one or more of the copolymers described herein and a selected bioactive agent. The bioactive agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The quantity and type of copolymers incorporated into the parenteral, ointment, gel, cream, etc., is variable. For a more viscous composition, a higher molecular weight polymer is used. If a less viscous composition is desired, a lower molecular weight polymer can be employed. The product may contain blends of the liquid or low melting point copolymers to provide the desired release profile or consistency to a given formulation.

While not essential for topical or transdermal administration of many drugs, in some cases, it may be preferred that a skin permeation enhancer be coadministered with the drug. Any number of the many skin permeation enhancers known in the art may be used. Examples of suitable enhancers include dimethylsulfoxide (DMSO), dimethylformamide (DMF), N,N-dimethylacetamide (DMA), deslymethylsulfoxide, ethanol, eucalyptol, lecithin, and the 1-N-dodecylcyclazacycloheptan-2-ones.

Depending on dosage form, the pharmaceutical compositions of the present invention may be administered in different ways, i.e. parenterally, topically, or the like. Preferred dosage forms are liquid dosage forms that can be administered parenterally.

The amount of bioactive agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of alkyd-lactone copolymer incorporated into the parenteral will vary depending on the release profile desired and the amount of drug employed. The product may contain blends of polymers to provide the desired release profile or consistency to a given formulation.

The alkyd-lactone copolymer, upon contact with body fluids, including blood or the like, undergoes gradual degradation, mainly through hydrolysis, with concomitant release of the dispersed drug for a sustained or extended period, as compared to the release from an isotonic saline solution. This can result in prolonged delivery of effective amounts of drug, e.g. over about 1 to about 2,000 hours, preferably about 2 to about 800 hours, or, e.g. 0.0001 mg/kg/hour to 10 mg/kg/hour. This dosage form can be administered as is necessary, depending on the subject being treated, the severity of the affliction, the judgment of the prescribing physician, and the like.

Individual formulations of drugs and alkyd-lactone copolymer may be tested in appropriate in vitro and in vivo models to achieve the desired drug release profiles. For example, a drug could be formulated with an alkyd-lactone copolymer and orally administered to an animal. The drug release profile could then be monitored by appropriate means, such as by taking blood samples at specific times and assaying the samples for drug concentration. Following this or similar procedures, those skilled in the art will be able to formulate a variety of formulations.

In a further embodiment of the present invention, the polymers and blends thereof can be used in tissue engineering applications, e.g. as supports for cells or delivery vehicle for cells. Appropriate tissue scaffolding structures are known in the art, such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art such as those methods disclosed in EPO 422 209 B1, WO 88/03785, WO 90/12604 and WO 95/33821, all of which are all hereby incorporated by reference herein as if set forth in their entirety.

The polymers of this invention can be melt-processed by numerous methods to prepare a vast array of useful devices. These polymers can be injection or compression molded to make implantable medical and surgical devices, especially wound closure devices. The preferred wound closure devices are surgical clips, staples and sutures.

Alternatively, the alkyd-lactone copolymers can be extruded to prepare filaments. The filaments thus produced may be fabricated into sutures or ligatures, attached to surgical needles, packaged, and sterilized by known techniques. The polymers of the present invention may be spun as monofilament or multifilament yarn and woven or knitted to form sponges or gauze, or used in conjunction with other molded compressive structures as prosthetic devices within the body of a human or animal where it is desirable that the structure have high tensile strength and desirable levels of compliance and/or ductility. Non-woven sheets also may be prepared and used as described above. Useful embodiments include tubes, including branched tubes, for artery, vein or intestinal repair, nerve splicing, tendon splicing, sheets for taping-up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of this invention includes solvent casting, particularly for those applications where a drug delivery matrix is desired. In more detail, the surgical and medical uses of the filaments, films, and molded articles of the present invention include, but are not limited to, knitted products, woven or non-woven, and molded products including, but not limited to burn dressings, hernia patches, meshes, medicated dressings, fascial substitutes, gauze, fabric, sheet, felt or sponge for liver hemostasis, gauze bandages, arterial graft or substitutes, bandages for skin surfaces, suture knot clip, orthopedic pins, clamps, screws, plates, clips, e.g. for vena cava, staples, hooks, buttons, snaps, bone substitutes, e.g. as mandible prosthesis, intrauterine devices, e.g. as spermicidal devices, draining or testing tubes or capillaries, surgical instruments, vascular implants or supports, e.g. stents or grafts, or combinations thereof, vertebral discs, extracorporeal tubing for kidney and heart-lung machines, artificial skin, and supports for cells in tissue engineering applications.

In another embodiment, the alkyd-lactone copolymer is used to coat a surface of a medical device to enhance the lubricity of the coated surface. The polymer may be applied as a coating using conventional techniques. For example, the polymer may be solubilized in a dilute solution of a volatile organic solvent, such as acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

It is contemplated that numerous surgical articles, including but not limited to endoscopic instruments, suture anchors, sutures, staples, surgical tacks, clips, plates, screws, drug-delivery devices, can be coated with the polymers of this invention to improve the surface properties of the article. The preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, including L-lactide D-lactide, meso-lactide and rac-lactide, ε-caprolactone, p-dioxanone, 1,4-dioxanone, 1,4-dioxepan-2-one, 1,5-dioxepan-2-one and trimethylene carbonate. The preferred suture is a braided multifilament suture composed of polyglycolide or poly(glycolide-co-lactide).

The amount of coating polymer to be applied on the surface of a braided suture can be readily determined empirically and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 weight percent. If the amount of coating on the suture were greater than about 30 weight percent, then it may increase the risk that the coating may flake off when the suture is passed through tissue.

Sutures coated with the polymers of this invention are desirable because they have a more slippery feel, thus making it easier for the surgeon to slide a knot down the suture to the site of surgical trauma. In addition, the suture is more pliable and, therefore, is easier for the surgeon to manipulate during use. These advantages are exhibited in comparison to sutures which do not have their surfaces coated with the polymer of this invention.

In another embodiment of the present invention, when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In another embodiment of the present invention, the solid polymers derived from alkyd-lactone copolymers can be used to overcoat microparticles encapsulating a bioactive agent(s). This would help provide an additional barrier for sustained release of the drug.

In yet another embodiment, the polymer comprises a bone replacement material comprising the solid polymer or a liquid polymer or a microdispersion and inorganic filler. The inorganic filler may be selected from alpha-tricalcium phosphate, beta-tricalcium phosphate, calcium carbonate, barium carbonate, calcium sulfate, barium sulfate, hydroxyapatite, and mixtures thereof. In certain embodiments the inorganic filler comprises a polymorph of calcium phosphate. Preferably, the inorganic filler is hydroxyapatite. The bone replacement materials may further comprise a bioactive agent in a therapeutically effective amount, such a growth factor, to facilitate growth of bone tissue. Furthermore, the bone replacement material may comprise a biologically derived substance selected from the group consisting of demineralized bone, platelet rich plasma, bone marrow aspirate and bone fragments. The relative amounts of polymer and inorganic filler may be determined readily by one skilled in the art by routine experimentation after having the benefit of this disclosure.

The injectable microdispersions can be used for a variety of soft tissue repair and augmentation procedures. For example, the microdispersions can be used in facial tissue repair or augmentation, including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences, e.g. lips, brow, etc. Additionally, these injectable microdispersions can be used to restore or improve sphincter function, such as for treating stress urinary incontinence. Other uses of these injectable microdispersions may also include the treatment of vesicoureteral reflux (incomplete function of the inlet of the ureter in children) by subureteric injection and the application of these microdispersions as general-purpose fillers in the human,body.

Surgical applications for an injectable, biodegradable microdispersion include, but are not limited to, facial contouring, e.g. frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like; periurethral injection, including injection into the submucosa of the urethra along the urethra, at or around the urethral-bladder junction to the external sphincter; urethral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic effect. Surgical specialists who would use such a product include, but are not limited to, plastic and reconstructive surgeons; dermatologists; facial plastic surgeons, cosmetic surgeons, otolaryngologists; urologists; gynecologists; gastroenterologists; ophthalmologists; and any other physician qualified to utilize such a product.

Additionally, to facilitate the administration and treatment of patients with the inventive microdispersion, pharmaceutically active compounds or adjuvants can be administered therewith. Pharmaceutically active agents that may be coadministered with the inventive microdispersion include but are not limited to anesthetics, e.g. lidocaine; and anti-inflammatory, e.g. cortisone.

The microdispersion can be administered with a syringe and needle or a variety of devices. It is also envisioned that the microdispersion could be sold in the form of a kit comprising a device containing the microdispersion. The device having an outlet for said microdispersion, an ejector for expelling the microdispersion and a hollow tubular member fitted to the outlet for administering the microdispersion into an animal.

The dosage forms for the microdispersions of the invention are sustained-release parenterals, bioerodible ointments, gels, creams, and similar soft dosage forms.

The examples set forth below are for illustration purposes only and are not intended to limit the scope of the claimed invention in any way. Numerous additional embodiments within the scope and spirit of the invention will become readily apparent to those skilled in the art.

In the examples below, the synthesized polymers were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 mg. Samples were heated from room temperature to 100° C. at 10° C./minute; quenched to −40° C. at 30° C./minute followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software.

EXAMPLE 1

Synthesis of Poly(monostearoyl glycerol-co-succinate)

197.2 gms of monostearoyl glycerol were added to a dry 500 ml, single neck, round bottom flask. A stir bar was added and a nitrogen inlet adapter was attached. The reaction flask was placed in a room temperature oil bath and a nitrogen gas blanket was started. The flask was heated to 140° C., and 50.0 gms of succinic anhydride were added. The temperature was raised to 200° C. and maintained for 4 hours. After 4 hours the flask was removed from the oil bath to cool to room temperature. Once the solution crystallized, it was deglassed and cleaned to remove any glass fragments. The polymer was an amber colored solid.

DSC measurements found a melt temperature of 46.8° C., and a specific heat of 63.6 J/gm. GPC measurement determined a number average molecular weight of 1420, and a weight average molecular weight of 3500. The $^1$H NMR showed the following peaks: δ 0.86 triplet (3H), 1.26 multiplet (28H), 1.61 multiplet (2H), 2.30 multiplet (2H), 2.65 multiplet (4H), 4.16 multiplet (2H), 4.34 multiplet (2H), and 5.28 multiplet (2H).

EXAMPLE 2

Synthesis of Poly(monooleoyl glyceride-co-succinate)

33.0 gms of glyceryl monooleate were added to a dry 100 ml, single neck, round bottom flask. A stir bar was added and a nitrogen inlet adapter was attached. The reaction flask was placed into a room temperature oil bath and a nitrogen blanket was applied. The oil bath temperature was raised to 140° C. Once at 140° C., 8.42 gms of succinic anhydride were added. The temperature was raised to 200° C. and maintained for 3 hours at 200° C. The flask was removed from the oil bath and allowed to cool to room temperature. The polymer was a pale yellow, viscous liquid.

The polymer was purified by dissolving in Ethyl acetate (5 gms polymer in 20 mls EtOAc) and added to a separatory funnel. The solution was washed three times with 20 mls of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated to give a viscous yellow liquid. The polymer was dried in the vacuum oven, where the oven was set around 40° C., for 48–72 hours.

GPC measurement determined a number average molecular weight of 2,145, and a weight average molecular weight of 3,659.

EXAMPLE 3

Synthesis of Poly(monostearoyl glyceride-co succinate-co-glycolide)

In a glove box, 60 gms of poly(monostearoyl glycerol-co-succinate) made following the procedure of Example 1, 40 gms of glycolide and 24.3 µl of stannous octoate were transferred into an oven-dried 250 ml single neck round bottom flask equipped with a stainless steel mechanical stirrer and a nitrogen gas blanket. The reaction flask was placed into an oil bath set at 190° C. and held for 18 hours under nitrogen with stirring. The flask was cooled to room temperature, deglassed and cleaned to remove any glass fragments. The polymer was then devolatilized under vacuum at 80° C. for 72 hours to remove unreacted glycolide. The polymer was an amber colored solid.

DSC measurements found a melt temperature of 52.3° C., and a specific heat of 47.6 J/gm. The $^1$H NMR showed the following peaks: δ 0.86 triplet (3H), 1.26 multiplet (27H), 1.61 multiplet (2H), 2.30 multiplet (2H), 2.60 multiplet (3H), 4.20 multiplet (2H), 4.30 multiplet (2H), 4.70 multiplet (1H), 4.80 multiplet (2H), and 5.38 multiplet (2H).

EXAMPLE 4

Synthesis of Poly(monostearoyl glyceride-co succinate-co-lactide)

In a glove box, 60 gms of poly(monostearoyl glycerol-succinate) made following the procedure of Example 1, 40 gms of lactide and 20.7 µl of stannous octoate were transferred into an oven-dried 250 ml single neck round bottom flask equipped with a stainless steel mechanical stirrer and a nitrogen gas blanket. The reaction flask was placed into an oil bath set at 190° C. and held for 18 hours under nitrogen with stirring. The flask was cooled to room temperature, deglassed and cleaned to remove any glass fragments. The polymer was then devolatilized under vacuum at 80° C. for 72 hours to remove any unreacted lactide. The polymer was an amber colored solid.

DSC measurements found a melt temperature of 40.2° C., and a specific heat of 24.3 J/gm. GPC measurement determined a number average molecular weight of 1,784, and a weight average molecular weight of 8,805. The $^1$H NMR showed the following peaks: δ 0.86 triplet (3H), 1.26 multiplet (27H), 1.61 multiplet (14H), 2.30 multiplet (2H), 2.60 multiplet (4H), 4.20 multiplet (4H), and 5.20 multiplet (5H).

EXAMPLE 5

Synthesis of Poly(monostearoyl glyceride-co succinate-co-caprolactone)

In a glove box, 60 gms of poly(monostearoyl glycerol-succinate) made following the procedure of Example 1, 40 gms of epsilon-caprolactone and 24.3 µl of stannous octoate were transferred into an oven-dried 250 ml single neck round bottom flask equipped with a stainless steel mechanical stirrer and a nitrogen gas blanket. The reaction flask was placed into an oil bath set at 190° C. and held for 18 hours under nitrogen with stirring. The flask was cooled to room temperature, deglassed and cleaned to remove any glass fragments. The polymer was then devolatilized under vacuum at 80° C. for 72 hours to remove any unreacted caprolactone. The polymer was an amber colored solid.

DSC measurements found a melt temperature of 41.1° C., and a specific heat of 43.4 J/gm. GPC measurement determined a number average molecular weight of 2,623, and a weight average molecular weight of 20,814. The $^1$H NMR showed the following peaks: δ 0.86 triplet (3H), 1.26 multiplet (27H), 1.35 multiplet (5H), 1.61 multiplet (12H), 2.30 multiplet (7H), 2.60 multiplet (4H), 4.20 multiplet (2H), 4.05 multiplet (5H), 4.10 multiplet (2H), 4.24 multiplet (1H), and 5.25 multiplet (1H).

EXAMPLE 6

Synthesis of Poly(monooleooyl glyceride-co succinate-co-caprolactone-co-glycolide)

In a glove box, 60 gms of poly(monooleoylglyceride-co-succinate) made following the procedure of Example 2, 19.85 gms of epsilon-caprolactone, 20.15 gms of glycolide and 24.3 µl of stannous octoate were transferred into an oven-dried 250 ml single neck round bottom flask equipped with a stainless steel mechanical stirrer and a nitrogen gas blanket. The reaction flask was placed into an oil bath set at 190° C. and held for 18 hours under nitrogen with stirring. The flask was cooled to room temperature, deglassed and cleaned to remove any glass fragments. The polymer was then devolatilized under vacuum at 80° C. for 72 hours to remove unreacted glycolide and caprolactone. The polymer was an amber colored viscous liquid.

GPC measurement determined a number average molecular weight of 2,080, and a weight average molecular weight of 8,248. The $^1$H NMR showed the following peaks: δ 0.86 triplet (3H), 1.26 multiplet (23H), 1.61 multiplet (8H), 2.00 multiplet (4H), 2.23 multiplet (1H), 2.40 multiplet (1H), 2.65 multiplet (1H), 2.75 multiplet (1H), 4.20 multiplet (8H), 4.70 multiplet (5H), 5.30 multiplet (3H).

I claim:

1. A composition, comprising: a synthetic, biodegradable, biocompatible polymer comprising the reaction product of a polybasic acid or derivative thereof, a monoglyceride and a lactone monomer.

2. The composition of claim 1 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

3. The composition of claim 1 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

4. The composition of claim 3 wherein said polybasic acid derivative is succinic anhydride.

5. The composition of claim 3 wherein said polybasic acid is succinic acid.

6. The composition of claim 1 wherein said lactone monomer is selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

7. The composition of claim 1 wherein said polymer is branched.

8. The composition of claim 1 wherein said polymer comprises the reaction product of said monoglyceride, said lactone monomer, and at least two of said polybasic acids or derivatives thereof selected from the group consisting of succinic acid, succinic anhydride, malic acid, tartaric acid, citric acid, diglycolic acid and diglycolic anhydride.

9. The composition of claim 1 wherein said polymer comprises the reaction product of said polybasic acid or derivative thereof, said lactone monomer, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

10. The composition of claim 1 wherein said polymer comprises the reaction product of said monoglyceride, said polybasic acid or derivative thereof, and at least two lactone monomers selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

11. The composition of claim 1 wherein said polymer further comprises an end-capping moiety selected from the group consisting of alkyls, alkenyls, alkynyls, acrylates, methacrylates, amines, isocyanates and isothiocyanates.

12. The composition of claim 1, further comprising an effective amount of a bioactive agent.

13. The composition of claim 12 wherein said bioactive agent is selected from the group consisting of antiinfectives, analgesics, anorexics, antihelmintics, antiarthritics, antiasthmatics, anticonvulsants, antidepressants, antidiuretics, antidiarrheals, antihistamines, antiinflammatory agents, antimigraine preparations, antinauseants, antineoplastics, antiparkinsonism drugs, antipruritics, antipsychotics, antipyretics, antispasmodics, anticholinergics, sympathomimetics, xanthine derivatives, calcium channel blockers, beta-blockers, antiarrhythmics, antihypertensives, diuretics, vasodilators, central nervous system stimulants, decongestants, hormones, steroids, hypnotics, immunosuppressives, muscle relaxants, parasympatholytics, psychostimulants, sedatives, tranquilizers, naturally derived or genetically engineered proteins, growth factors, polysaccharides, glycoproteins, or lipoproteins, oligonucleotides, antibodies, antigens, cholinergics, chemotherapeutics, hemostatics, clot dissolving agents, radioactive agents and cystostatics.

14. The composition of claim 1 comprising a microdispersion, said microdispersion comprising a solid polymer phase dispersed in a liquid polymer phase, wherein one of said solid polymer and said liquid polymer comprise the reaction product of a polybasic acid or derivative thereof, a monoglyceride, and a lactone monomer; wherein said solid polymer has a melting point between about 25° C. and about 70° C., and wherein said liquid polymer has a melting point below about 25° C.

15. The composition of claim 13 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

16. The composition of claim 14 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

17. The composition of claim 15 wherein said polybasic acid derivative is succinic anhydride.

18. The composition of claim 15 wherein said polybasic acid is succinic acid.

19. The composition of claim 13 wherein said lactone monomer is selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

20. The composition of claim 13 further comprising an effective amount of a bioactive agent.

21. The composition of claim 13 wherein both said solid polymer and said liquid polymer comprise the reaction product of a polybasic acid or derivative thereof, a monoglyceride, and a lactone monomer.

22. A medical device comprising a coating, said coating comprising: a synthetic, biodegradable, biocompatible polymer comprising the reaction product of a polybasic acid or derivative thereof, a monoglyceride, and a lactone monomer.

23. The medical device of claim 22 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

24. The medical device of claim 22 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

25. The medical device of claim 24 wherein said polybasic acid derivative is succinic anhydride.

26. The medical device of claim 24 wherein said polybasic acid is succinic acid.

27. The medical device of claim 22 wherein said lactone monomer is selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

28. The medical device of claim 22 wherein said polymer is branched.

29. The medical device of claim 22 wherein said polymer comprises the reaction product of said monoglyceride, said lactone monomer, and at least two of said polybasic acids or derivatives thereof selected from the group consisting of succinic acid, succinic anhydride, malic acid, tartaric acid, citric acid, diglycolic acid and diglycolic anhydride.

30. The medical device of claim 22 wherein said polymer comprises the reaction product of said polybasic acid or derivative thereof, said lactone monomer, and at least two monoglycerides selected from the group consisting of monostearoyl glycerol, monopalmitoyl glycerol, monomyrisitoyl glycerol, monocaproyl, glycerol, monodecanoyl glycerol, monolauroyl glycerol, monolinoleoyl glycerol and monooleoyl glycerol.

31. The medical device of claim 22 wherein said polymer comprises the reaction product of said monoglyceride, said polybasic acid or derivative thereof, and at least two lactone monomers selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

32. The medical device of claim 22 wherein said polymer further comprises an end-capping moiety selected from the group consisting of alkyls, alkenyls, alkynyls, acrylates, methacrylates, amines, isocyanates and isothiocyanates.

33. The medical device of claim 22, further comprising an effective amount of a bioactive agent.

34. The medical device of claim 22 further comprising an aliphatic polyester prepared from the group of monomers selected from the group consisting of glycolide, L-lactide, D-lactide, meso-lactide, rac-lactide, ε-caprolactone, trimethylene carbonate, p-dioxanone, 1,4-dioxanone, 1,4-dioxepan-2-one, 1,5-dioxepan-2-one and substituted derivatives thereof.

35. A synthetic polymer comprising the reaction product of:
   a polybasic acid or derivative thereof;
   a monoglyceride; and
   a lactone monomer.

36. The polymer of claim 35 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters and acid halides.

37. The polymer of claim 35 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

38. The polymer of claim 37 wherein said polybasic acid derivative is succinic anhydride.

39. The polymer of claim 37 wherein said polybasic acid is succinic acid.

40. The polymer of claim 35 wherein said lactone monomer is selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

41. The polymer of claim 35 wherein said polymer is branched.

42. The polymer of claim 35 wherein said polymer comprises the reaction product of said monoglyceride, said lactone monomer, and at least two of said polybasic acids or derivatives thereof selected from the group consisting of succinic acid, succinic anhydride, malic acid, tartaric acid, citric acid, diglycolic acid and diglycolic anhydride.

43. The polymer of claim 35 wherein said polymer comprises the reaction product of said polybasic acid or derivative thereof, said lactone monomer, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

44. The polymer of claim 35 wherein said polymer comprises the reaction product of said monoglyceride, said polybasic acid or derivative thereof, and at least two lactone monomers selected from the group consisting of glycolide, d-lactide, l-lactide, meso-lactide, epsilon-caprolactone, para-dioxanone, trimethylene carbonate, 1,4 dioxepan-2-one, and 1,5 dioxepan-2-one.

* * * * *